United States Patent
Wang

(10) Patent No.: US 12,262,982 B2
(45) Date of Patent: Apr. 1, 2025

(54) SYSTEMS AND METHODS FOR DETECTING SMALL PHYSIOLOGICAL OR PATHOLOGICAL CHANGES USING HIGH RESOLUTION MAGNETIC RESONANCE IMAGING

(71) Applicant: University of Cincinnati, Cincinnati, OH (US)

(72) Inventor: Jinghua Wang, Mason, OH (US)

(73) Assignee: University of Cincinnati, Cincinnati, OH (US)

( * ) Notice: Subject to any disclaimer, the term of this patent is extended or adjusted under 35 U.S.C. 154(b) by 537 days.

(21) Appl. No.: 16/648,377

(22) PCT Filed: Sep. 18, 2018

(86) PCT No.: PCT/US2018/051413
§ 371 (c)(1),
(2) Date: Mar. 18, 2020

(87) PCT Pub. No.: WO2019/060258
PCT Pub. Date: Mar. 28, 2019

(65) Prior Publication Data
US 2020/0281500 A1    Sep. 10, 2020

Related U.S. Application Data

(60) Provisional application No. 62/560,370, filed on Sep. 19, 2017.

(51) Int. Cl.
*A61B 5/055* (2006.01)
*G01R 33/48* (2006.01)
*G01R 33/561* (2006.01)

(52) U.S. Cl.
CPC .......... *A61B 5/055* (2013.01); *G01R 33/4818* (2013.01); *G01R 33/5611* (2013.01)

(58) Field of Classification Search
CPC ............... A61B 5/055; G01R 33/4818; G01R 33/5611; G01R 33/5613
See application file for complete search history.

(56) References Cited

U.S. PATENT DOCUMENTS

| 7,012,428 B1 | 3/2006 | Ward et al. |
| 7,030,609 B2 | 4/2006 | Pipe |

(Continued)

FOREIGN PATENT DOCUMENTS

| JP | 2003325477 A | 11/2003 |
| WO | 2004021881 A1 | 3/2004 |

(Continued)

OTHER PUBLICATIONS

Zhao B, Haldar JP, Image reconstruction from highly undersampled (k, t)-space data with joint partial separability and sparsity constraints. IEEE Trans Med Imaging. Sep. 2012;31(9):1809-20. doi: 10.1109/TMI.2012.2203921. Epub Jun. 8, 2012. PMID: 22695345; PMCID: PMC3434301. (Year: 2012).*

(Continued)

*Primary Examiner* — Joseph M Santos Rodriguez
*Assistant Examiner* — Zainab Mohammed Aldarraji
(74) *Attorney, Agent, or Firm* — Dinsmore & Shohl LLP

(57) ABSTRACT

A method for obtaining a magnetic resonance imaging (MRI) image of an object is provided. The method includes applying a MRI sequence to a target area in the object, receiving magnetic resonance (MR) signals from the target area, acquiring, in one k-space strategy, a first set of k-space lines based on the MR signals while nuclear spins in the target area are in a transient state, acquiring, in another k-space strategy, a second set of k-space lines based on the MR signals while the nuclear spins in the target area are in a steady-state or a mixed state of the transient state and the (Continued)

steady-state, and reconstructing the MRI image based on the first set of k-space lines and the second set of k-space lines.

18 Claims, 9 Drawing Sheets

(56) References Cited

U.S. PATENT DOCUMENTS

| | | | |
|---|---|---|---|
| 7,834,629 B2 | 11/2010 | Doyle | |
| 8,280,482 B2 | 10/2012 | Rusinek et al. | |
| 8,299,788 B2 | 10/2012 | Wheaton | |
| 8,340,381 B2 | 12/2012 | Franaszek et al. | |
| 8,368,398 B2 | 2/2013 | Griswold et al. | |
| 8,384,384 B2 | 2/2013 | Zhao et al. | |
| 8,971,657 B2 | 3/2015 | Tseng et al. | |
| 9,339,239 B2 | 5/2016 | Wang et al. | |
| 9,747,702 B2 | 8/2017 | Heismann | |
| 10,552,955 B2* | 2/2020 | Hu | G06T 11/006 |
| 2010/0273205 A1 | 10/2010 | Blackwell et al. | |
| 2013/0106417 A1 | 5/2013 | Nakanishi et al. | |
| 2013/0190605 A1 | 7/2013 | Annapragada et al. | |
| 2015/0185303 A1* | 7/2015 | Umeda | G01R 33/482 324/309 |
| 2016/0313427 A1* | 10/2016 | Ennis | G01R 33/5602 |
| 2017/0046826 A1 | 2/2017 | Konen et al. | |
| 2017/0189565 A1 | 7/2017 | Miller et al. | |
| 2018/0045799 A1* | 2/2018 | Wang | A61B 5/055 |
| 2018/0286041 A1* | 10/2018 | Hu | G01R 33/5611 |
| 2022/0221540 A1* | 7/2022 | Fair | G01R 33/5608 |

FOREIGN PATENT DOCUMENTS

| | | |
|---|---|---|
| WO | 2009013650 A2 | 1/2009 |
| WO | 2013024257 A1 | 2/2013 |
| WO | 2014107651 A1 | 7/2014 |
| WO | 2015112804 A1 | 7/2015 |
| WO | 2016145355 A1 | 9/2016 |
| WO | 2017040538 A1 | 3/2017 |

OTHER PUBLICATIONS

Extended European Search Report pertaining to corresponding European Patent Application No. 18858833.9 dated Apr. 26, 2021.
International Search Report & Written Opinion to corresponding PCT Application No. PCT/US2018/051413 dated Nov. 21, 2018.

* cited by examiner

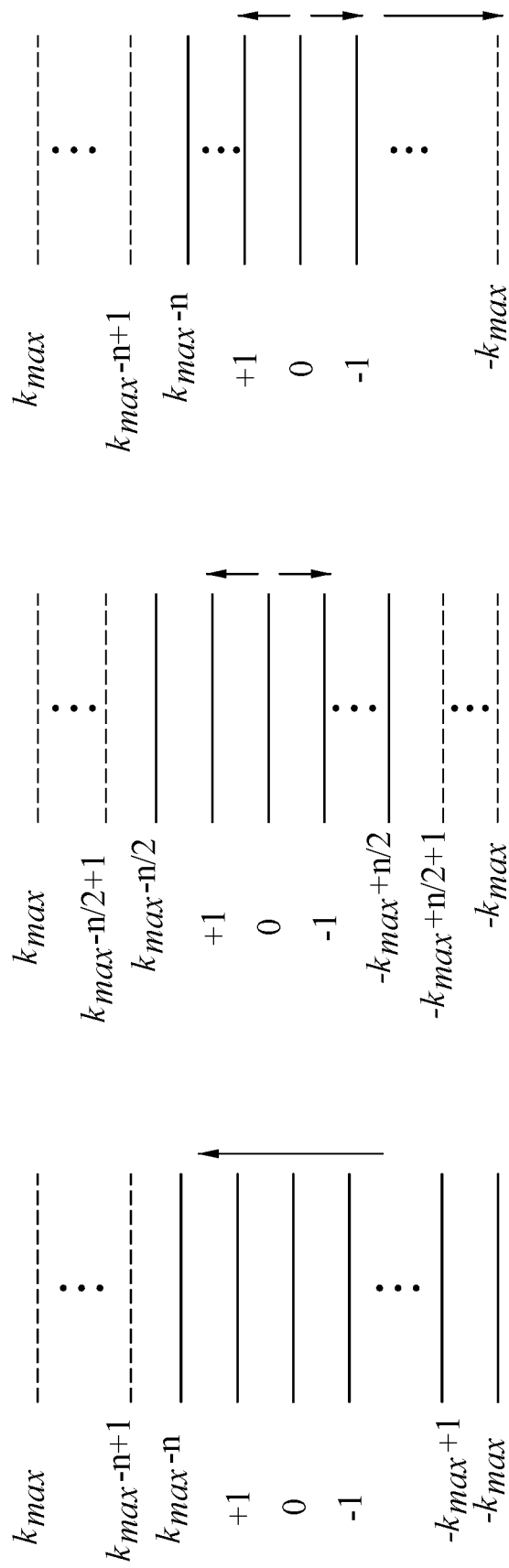

SYSTEMS AND METHODS FOR DETECTING SMALL PHYSIOLOGICAL OR PATHOLOGICAL CHANGES USING HIGH RESOLUTION MAGNETIC RESONANCE IMAGING

CROSS-REFERENCE TO RELATED APPLICATIONS

The present application is a national phase of International Application No. PCT/US2018/51413 filed on Sep. 18, 2018 which claims the benefit of U.S. Provisional Application No. 62/560,370 filed on Sep. 19, 2017, the entire contents of which are incorporated by reference.

BACKGROUND

1. Field of the Invention

The present invention relates to systems and methods for detecting small physiological and pathological changes using high-resolution magnetic resonance imaging (MRI) with hybrid k-space acquisition.

2. Description of the Related Art

Magnetic resonance imaging (MRI) is one of the most important modern medical imaging modalities. It has far less risk of side effects than most other imaging modalities such as radioscopy with x-rays or computed tomography because patients and medical personnel are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnosis of various diseases, such as tumors, strokes, heart problems, and spine diseases. A high-quality scan is important for maximizing diagnostic sensitivity and accuracy. Generally, high quality images are characterized by high signal to noise ratio (SNR), high contrast between normal and pathological tissues, low levels of artifacts, and appropriate spatial-temporal resolution In order to obtain a detectable magnetic resonance (MR) signal, the object/subject examined is positioned in a homogeneous static magnetic field so that the object's nuclear spins generate net magnetization oriented along the static magnetic field. The net magnetization is rotated away from the static magnetic field using a radio frequency (RF) excitation field with the same frequency as the Larmor frequency of the nucleus. The angle of rotation is determined by the field strength of the RF excitation pulse and its duration. In the end of the RF excitation pulse, the nuclei, in relaxing to their normal spin conditions, generate a decaying signal (the "MR signal") at the same radio frequency as the RF excitation. The MR signal is picked up by a receive coil, amplified and processed. The acquired measurements, which are collected in the spatial frequency domain, are digitized and stored as complex numerical values in a "k-space" matrix. An associated MR image can be reconstructed from the k-space data, for example, by an inverse 2D or 3D fast Fourier transformation (FFT) from the raw k-space data.

In the k-space data, most MR image information (e.g., contrast, general object shape) is contained in the low-spatial-frequency components (e.g., center of k-space). In other words, the highest amplitudes in low-spatial-frequency components give rise to the greatest changes in image contrast. Although high-spatial-frequency components in the periphery of the k-space have little effect on image contrast or general shape, these components are important for image sharpness because they encode edge information. The higher the spatial frequency the k-space covers, the higher the spatial resolution of the image. Therefore, it is necessary to obtain the k-space data at the higher spatial frequency in k-space domain to achieve higher spatial resolution in image domain.

MRI sequences, such as $T_1$-weighted and $T_2$-weighted sequences, can be used in 2 dimensional (2D) or 3 dimensional (3D) acquisition mode. 3D sequences have generally higher signal-to-noise ratios, reformatted orientation and can acquire higher spatial resolution images that are desirable for neuroimaging, especially in structural MRI imaging. The main disadvantage of 3D acquisition is long acquisition times that make it sensitive to motion. This can cause undesired effects like mis-registration, and furthermore limits the field of view. Currently, MRI scanners provide MRI images of internal features in target region having spatial resolution of more than 1 $mm^3$ (cubic millimeter) in clinical practices. The high resolution can show a high level of anatomical detail and have a potential for non-invasive in vivo brain MRI histology, otherwise impossible to obtain with traditional histology. The higher spatial resolution leads to a potentially more accurate segmentation due to reduced partial volume effects and lower the error in estimating or detecting target tissues or lesions. Additionally, higher resolution MRI image leads to higher detection sensitivity for small pathologic changes in brain structure. Finally, MRI image with sub-millimeter resolution may have a potential to partly replace histology for brain anatomy. However, high-resolution imaging of the living human body faces many challenges: resolution, scan time, contrast and SNR describe the limiting factors of an MRI scan. The SNR of the MR data and of the resulting image is proportional to the voxel volume. Hence, SNR is decreasing for higher resolutions. At high resolution, more voxels are needed to cover the same target region, which increases phase-encoding steps and result in total long scan time. Generally, the total scan time is proportional to the number of the phase-encoding steps. For example, a magnetization prepared rapid gradient-echo (MP-RAGE) sequence used to acquire a whole brain coverage image with the resolution of 0.7×0.7× 0.74 $mm^3$ will take total acquisition time of 8 minutes and 58 seconds at 7.0 Tesla. Whole Brain coverage image with sub-millimeter resolution is rare in clinical practices because of long scan time and low image quality at 1.5 and 3.0 Tesla. There is a critical need for obtaining high resolution MRI image with reasonable scan time. That is, it is needed to develop a method and apparatus, such as ultra-high field MRI, compressed sense, and phased array coils, to achieve high image quality with a better spatial-temporal resolution in a short time.

The history of imaging technique in medicine, hybrid techniques which have their own merits and demerits have been widely used for the fusion of two or more techniques to yield the complementary information which the other could not afford to provide. Hybrid (multimodal or fusion) imaging is an integrated technology that combines functional/molecular imaging and structure imaging technologies. The strengths of each modality synergistically complement each other to create a new and more powerful tool, overcoming their stand-alone limitations. For example, the combination of positron emission tomography (PET) and MRI provides the unique features of soft tissue contrast and various functional imaging parameters provided by MR with high sensitivity and quantification of radiotracer metabolism provided by positron emission tomography. As a result, the combination of PET with MRI provides many advantages that go far beyond simply combining functional PET as described in following references.

WO 2009/013650 A3 and U.S. Pat. No. 8,525,116 B2 to Volkmar Shultz et al. disclose a PET/MRI hybrid machine that combines a PET device with an MRI device for medical imaging. It is a type of the hybrid of different image modalities.

Moreover, hybrid ideal or concept has also been widely used for the development of MRI techniques to realize the full potential of MR imaging as described in following references.

U.S. Pat. No. 7,834,629 B2 to Mark Doyle discloses an MRI scanner which comprises of hybrid configuration of a cylindrical housing, receiver coil system, and gradients coil system. It is a type of the hybrid of scanner configuration.

U.S. Pat. No. 8,340,381 B2 to Marek Franaszek and Ronald M. Summers discloses a hybrid segmentation method for anatomical structure.

U.S. Pat. No. 8,299,788 B2 to Andrew J Wheaton discloses MRI processes to obtain a hybrid image (e.g., a hybrid dark artery image) based on plural images acquired with different imaging parameters. It is a type of the hybrid of different MR images.

WO 2013/024257 A1 to Mcginley et al. discloses a hybrid magnet for an MRI scanner.

U.S. Pat. No. 8,368,398 B2 to Mark A Griswold et al. discloses a hybrid k-space MRI acquisition which combines Cartesian and non-Cartesian segments that sample that sample in a manner that satisfies the Nyquist criterion in at least one region of a volume to be imaged. It is a type of the hybrid of K-space trajectory.

U.S. Pat. No. 7,030,609 B2 to James G Pipe discloses a propeller MRI (a hybrid k-space MRI acquisition) which combines rectangle and radial k-space trajectory acquisition together to reduce the motion artifacts in MRI acquisition. It is also a type of the hybrid of k-space trajectory.

U.S. Pat. No. 8,384,384 B2 to Xiaoli Zhao et al. discloses a revised propeller MRI which each blade may have orientations at different angles from one another. It is also a type of the hybrid of K-space trajectory.

U.S. Pat. No. 9,339,239 B2 to Jinghua Wang et al. discloses a method to optimize the central k-space acquisition for the improvement of image quality. The disclosure focused on the low frequency components of k-space domain.

WO 2016/145355 Jinghua Wang et al. discloses a method and system to optimize acquisition train length (e.g. number of k-space acquisition) to improve image quality. The disclosure focused on reducing the k-space number with partial Fourier acquisition to improve the image quality for echo train acquisition.

WO 2014/107651 A1 and U.S. Pat. No. 9,629,602 B2 to Synho Do et al. discloses a method for non-uniform sampling schemes based on general k-space trajectory in order to improve acquisition speed or sampling density. The method combined non-uniform sampling with advanced reconstruction methods to reduce data sampling and mitigate under-sampling artifacts and motion artifacts.

U.S. Pat. No. 8,280,482 B2 to Megan L. Blackwell et al. discloses that higher magnetic field strengths and more powerful gradient systems developed in recent years have resulted in increased signal-to-noise ratios (SNR) in magnetic resonance (MR) images. The increased SNR may be used to acquire images of high resolution, even including isotropic voxels around 1 mm for in vivo objects.

The spatial-temporal resolution is very critical for the detection of small physiological and pathological changes. For example, US 2017/0046826 to Konen, E., et al. discloses providing relatively high quality, high resolution intraoperative MRI images, hereinafter also referred to as "hiQ-iMRI" images, of a target site in a body at which an invasive medical procedure is being performed that are substantially contemporaneous with performance of the medical procedure at the two different scanners.

U.S. Pat. No. 8,280,482 B2 to Henry Rusinek et al. discloses methods for measuring brain atrophy in the hippocampus and entorhinal cortex. The method can characterize loss of brain volume in medial-temporal lobe and are compared with normative brain loss due to aging. Abnormally high rate of brain loss can be used for diagnosis of neurodegenerative diseases. The proposed method really reduce partial volume, but the relatively low spatial resolution of around 1.3 $mm^3$ still limit the accuracy of estimating brain atrophy in the hippocampus and entorhinal cortex.

WO 2015/112804 A1 and U.S. Pat. No. 9,629,602 B2 to Kourosh Jafari-Lhouzani disclose a system and method for generating high resolution images from low resolution images or data by selectively choosing neighbors and the tissue types of the neighbors when estimating the image intensity of a voxel with the values of the neighbors. The method interpolates low-resolution images of a first contrast with the help of the high-resolution images of a second contrast using the anatomical structures. The invention is useful at which spatial resolution can be compromised to achieve reasonable scan time and minimize the likelihood of motion artifact, for example, in dynamic contrast enhanced and dynamic susceptibility contrast MRI of brain.

U.S. Pat. No. 8,971,657 B2 to Fan-Pin Tseng et al. discloses a method to reduce blur phenomenon caused by partial volume effects and improve image accuracy through operation of iterated algorithm. The invention applies the technique of image restoration for image quality enhancement, whereas such image restoration technique strongly depends on the algorithm and cannot reduce partial volume effects greatly.

US 2017/0189565 to Matthew Miller et al. discloses a method to use of anti-1-amino-3-$^{18}$F-fluorocyclobutane-1-carboxylic acid (FACBC) in PET for imaging, diagnosing and monitoring brain metastasis or recurrence of cancer at the resolution of 7 mm or less. Herein, high-resolution contrast enhanced MRI for diagnosing and monitoring brain metastasis or recurrence of cancer at the resolution of around 1 mm or less than.

U.S. Pat. No. 9,747,702 B2 to Bjoern Heismann discloses a high-resolution magnetic resonance image dataset of at least one limited body region having at least one anatomical structure of a patient. The resolution for disclosure is at least one pixel per millimeter of the at least one anatomical structure of the at least one limited body region.

WO 2017/040538 to Jin Hyung Lee et al. discloses a methods and systems for high-resolution functional magnetic resonance imaging (fMRI), including real-time high-resolution functional MRI methods and systems.

SUMMARY

The patents mentioned above mainly focus on hybrid of hardware and image modalities to improve the image quality. Several patents focus on the technology and method of hybrid of k-space trajectories. However, no references concentrate on the hybrid of k-space ordering to improve the image quality, particularly for optimized k-space sample ordering of both transient state and steady state acquisition. As for image analysis, the patents mentioned above mainly focus on reducing partial volume effect and improving detection sensitivity of target tissues. There are known difficulties to obtain high-resolution image with enough contrast and signal with clinically acceptable scan time is challenging at 1.5 and 3.0 Tesla. Additionally, other factors, such as the acquisition time, short physiological phenomena, and organ motion also limit the acquisition and application of an image with high spatial resolution. The present disclosure improves the image quality throughout the optimization of k-space acquisition in both transient state and steady state so that spatial signal-to-noise ratio and contrast-to-noise ratio efficiencies for a given voxel size is greatly improved. The increased spatial signal-to-noise ratio and contrast-to-noise ratio efficiencies can be used to increase the spatial resolution of image in clinically acceptable scan time or a given scan time. The increased spatial resolution improves the influence of partial volume effect so that the small target tissue can be detectable and/or estimated accurately.

Disclosed herein is an optimized hybrid k-space strategy for acquiring high quality MRI images. For example, the present disclosure describes a method for combining sequential view k-space sampling order or reversal sequential view k-space sampling order and central view k-space view for the improvement of image quality.

In one embodiment, a method for obtaining a magnetic resonance imaging (MRI) image of an object is provided. The method includes applying a MRI sequence to a target area in the object, receiving magnetic resonance (MR) signals from the target area, acquiring, in one k-space strategy, a first set of k-space lines based on the MR signals while nuclear spins in the target area are in a transient state, acquiring, in another k-space strategy, a second set of k-space lines based on the MR signals while the nuclear spins in the target area are in a steady-state or a mixed state of the transient state and the steady-state, and reconstructing the MRI image based on the first set of k-space lines and the second set of k-space lines. The transient state may exist in an echo train acquisition such as a series of radiofrequency pulses acquisition (e.g., MP-RAGE), refocusing radiofrequency pulse acquisition (e.g., fast echo spin), and bipolar gradient acquisition (e.g., echo planar imaging).

In another embodiment, a system for obtaining a magnetic resonance imaging (MRI) image of an object is provided. The system includes a magnetic field generating unit configured to apply a MRI sequence to a target area in the object, a receiver configured to receive MR signals from the target area, a processing unit, a system memory, and machine readable instructions stored in the system memory that, when executed by the processing unit, cause the processing unit to: acquire, in one k-space strategy, a first set of k-space lines based on the MR signals while nuclear spins in the target area are in a transient state, acquire, in another k-space strategy, a second set of k-space lines based on the MR signals while the nuclear spins in the target area are in a steady-state or a mixed state of the transient state and the steady-state, and reconstruct the MRI image based on the first set of k-space lines and the second set of k-space lines.

In yet another embodiment, a method for detecting pathological or structural changes using magnetic resonance imaging (MRI) of an object is provided. The method includes acquiring an MRI image of a target region in the object with a method of the present disclosure, differentiating pathological or structural changes from normal physiological changes of the target region in the object based on the acquired MRI image, and characterizing pathological changes.

These and other objects, features, embodiments, and advantages will become apparent to those of ordinary skill in the art from a reading of the following detailed description and the appended claims.

BRIEF DESCRIPTION OF THE DRAWINGS

The components in the drawings are not necessarily to scale relative to each other. Like reference numerals designate corresponding parts throughout the several views.

FIG. 4A depicts an example of sequential k-space view sampling schedules for MRI sequence with the partial Fourier acquisition;

FIG. 4B depicts an example of central k-space view sampling schedules for MRI sequence with the partial Fourier acquisition;

FIG. 4C depicts an example of hybrid k-space view sampling schedules for MRI sequence with the partial Fourier acquisition;

DETAILED DESCRIPTION

Figure 1:
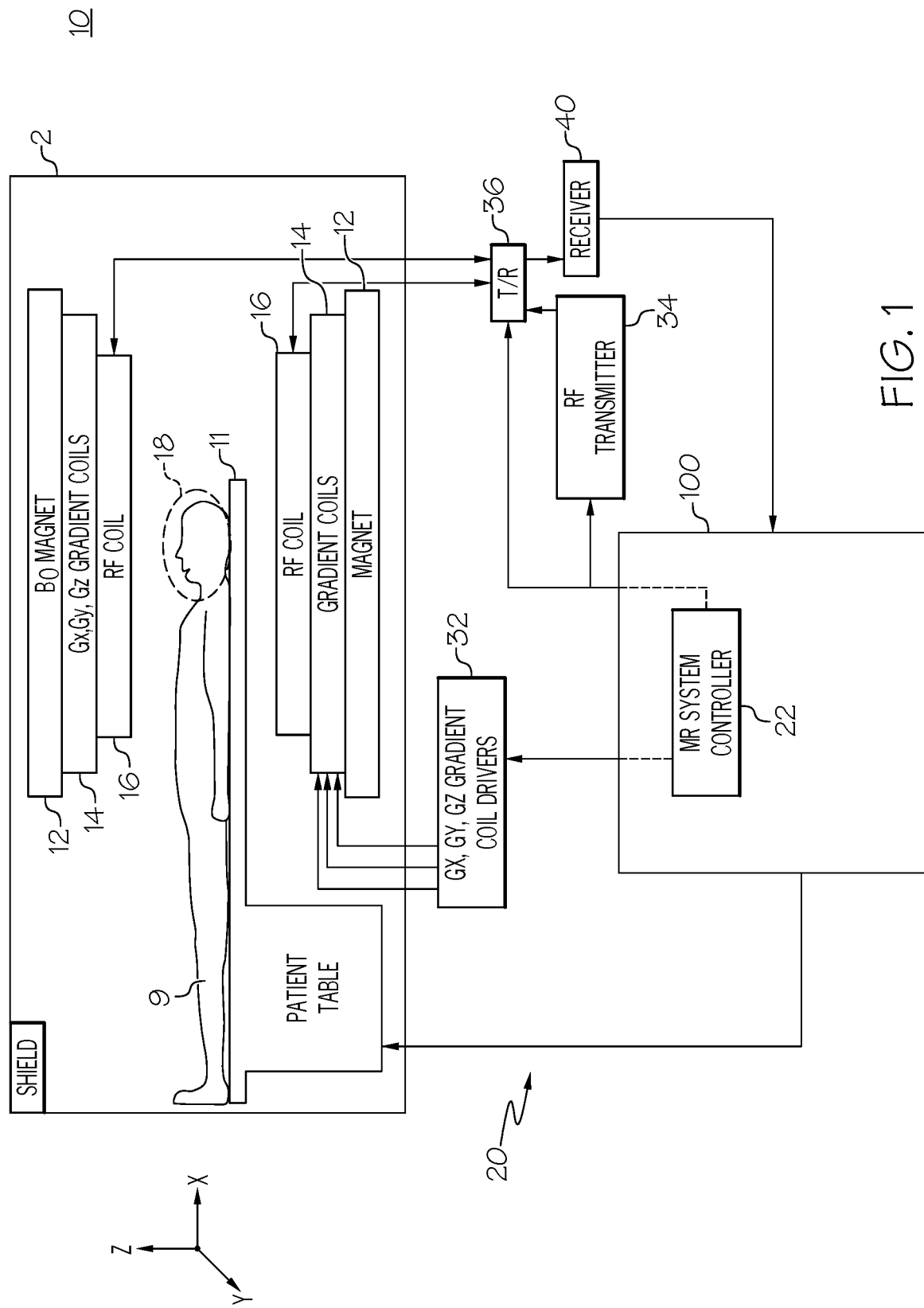
FIG. 1 depicts an MRI system, according to one or more embodiments described and shown herewith.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "the" include plural referents unless the context dearly dictates otherwise. The "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for optimizing MRI scanner settings (also referred to herein as "basic scanner settings"), MRI protocols, variable flip angle, k-space strategy, and/or imaging parameters with regard to MRI modalities, it will become evident to those skilled in the art that the implementations are not limited thereto, but are applicable to other image modalities such as, computed tomography, for example. Additionally, this disclosure contemplates that MRI modalities include MRI techniques with administration of contrast agents, for example, contrast enhanced MR angiography. This disclosure contemplates that the images obtained using the techniques described herein can be directly employed in at least one of diagnosing diseases, monitoring prognosis and therapeutic responses, conducting treatment plans, and improving quantification of MRI. For example, the techniques described herein can be used for the diagnoses of specific diseases such as the standardization of the MRI protocol in The Alzheimer's Disease Neuroimaging Initiative, Additionally, the techniques described herein are optionally applicable to a group of individuals in a similar pathophysiological situation.

The term "target tissue" and variations thereof as used herein include at least one of normal tissue, lesion and their combination.

The term "k-space" and variations (such as frequency domain or raw data) thereof as used herein indicate the data space in which MRI raw data is acquired. The k-space represents the spatial frequency information in two or three dimensions of an object. The k-space is defined as a space covered by the phase and frequency encoding data. In contrast to this, the Fourier-transformed counterpart of the k-space is defined as an image space or image domain. The relationship between k-space data and image data is the Fourier transformation. Each data point in k-space represents a different superposition of the tissue signals. Every point in the raw data matrix contains part of the information for the complete image. A point in the raw data matrix does not correspond to a point in the image matrix. The high spatial frequency components provide information about the borders and contours of the image, the detail of the structures. The low spatial frequency components provide information on the general contrast of the image.

The term "multiple partition k-space" thereof as used herein indicate that k-space are classified into multiple partitions which each partition has their own k-space strategy. The k-space strategy includes, but not limited to, k-space sampling order, k-space trajectory, k-space under sampling, partial k-space acquisition and their combinations or hybrid. For example, multi-sequential k-space sampling view orders (from $-k_{max}$ to $+k_{max}$) can be classified into the sum of the first acquisition (from the beginning of k=0 to the end of k=$-k_{max}$) and the second acquisition (from the beginning of k=$+k_{max}$ to the end of k=1 or 0).

The term "transient state" and variations thereof as used herein indicate that the state of nuclear spin evolution in MRI experiments has been changed in a transient state before the state has not yet reached a steady state.

The term "a steady state" and variations thereof as used herein indicate that the state of nuclear spin evolution in MRI experiments has reached a steady state and MRI signal is maintained between successive k-space acquisitions.

The term "pixel" and variations thereof as used herein indicates a picture element in a two-dimensional image element.

The term "voxel" and variations thereof as used herein indicates a picture element in a three-dimensional image element.

The term "noise" and variations thereof as used herein indicate image noise that is random variation of signal intensity, and is usually an aspect of white noise or electronic noise. The noise (μ) in MRI is an important parameter in image processing and analysis. For example, a simple approach for estimating the noise is directly performed from noise region that contains only air. It is given by:

$$\mu = 1.515 * \sigma \qquad (1)$$

where σ is the standard deviation of the noise, which is estimated from a large area that contains only air. 1.515 is a correction factor that takes into account the fact that the noise is governed by the Rayleigh distribution.

The term "signal-to-noise (SNR)" is used in imaging as a physical measure of the sensitivity of an imaging system which is defined as:

$$SNR = S/\mu = \frac{0.66 \cdot S}{\sigma} \qquad (2)$$

where S is the mean signal intensity from the reference region, and 0.66 is a correction factor that takes into account the fact that the noise is governed by the Rayleigh distribution.

As used herein, contrast is defined as:

$$\text{Contrast} = \mu_A - \mu_B, \qquad (3)$$

where $\mu_A$ and $\mu_B$ are the average signal value of regions A and B, respectively. It should be understood that other definitions of contrast can also be used as the objective function, such as Weber contrast and Michelson contrast, for example.

The term "contrast-to-noise (CNR) is used as a metric to determine image quality, and is defined as:

$$CNR = \text{Contrast}/\mu; \qquad (4)$$

The term "signal-to-noise (SNR) efficiency" and variations thereof as used herein $SNR_{eff}$, is defined as SNR per square root total scan time TA:

$$SNR_{eff} = SNR/\sqrt{TA} \qquad (5)$$

The term "contrast-to-noise (CNR) efficiency" and variations thereof as used herein $CNR_{eff}$, is defined as CNR per square root total scan time TA:

$$CNR_{eff} = CNR/\sqrt{TA} \qquad (6)$$

The term "spatial SNR efficiency" $SP\_SNR_{eff}$ and variations thereof as used herein is defined as $SNR_{eff}$ per voxel:

$$SP\_SNR_{eff} = SNR_{eff}/V \qquad (7)$$

where V is a volume of the voxel.

The term a spatial CNR efficiency and variations thereof as used herein is defined as $CNR_{eff}$ per voxel:

$$SP\_CNR_{eff} = CNR_{eff}/V \qquad (8)$$

These metric are estimated based on the same coverage image. That is, the number of slice is identical or very close. If the number of slice is different, the term "a slice spatial SNR efficiency" and variations should be introduced to describe the efficiency by replacing the total scan time TA with scan time of per slice TS is given by:

$$SP\_SNR_{eff\text{-}slice} = SNR/(V \cdot \sqrt{TA/n}) \qquad (9)$$

where n is the number of acquired slices at the total scan time TA.

Similarly, the term "a slice spatial CNR efficiency" and variations should be given by:

$$SP\_CNR_{\textit{eff-slice}} = CNR/(V\sqrt{TA/n}) \tag{10}$$

MRI System Overview

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals. The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

Figure 1A:
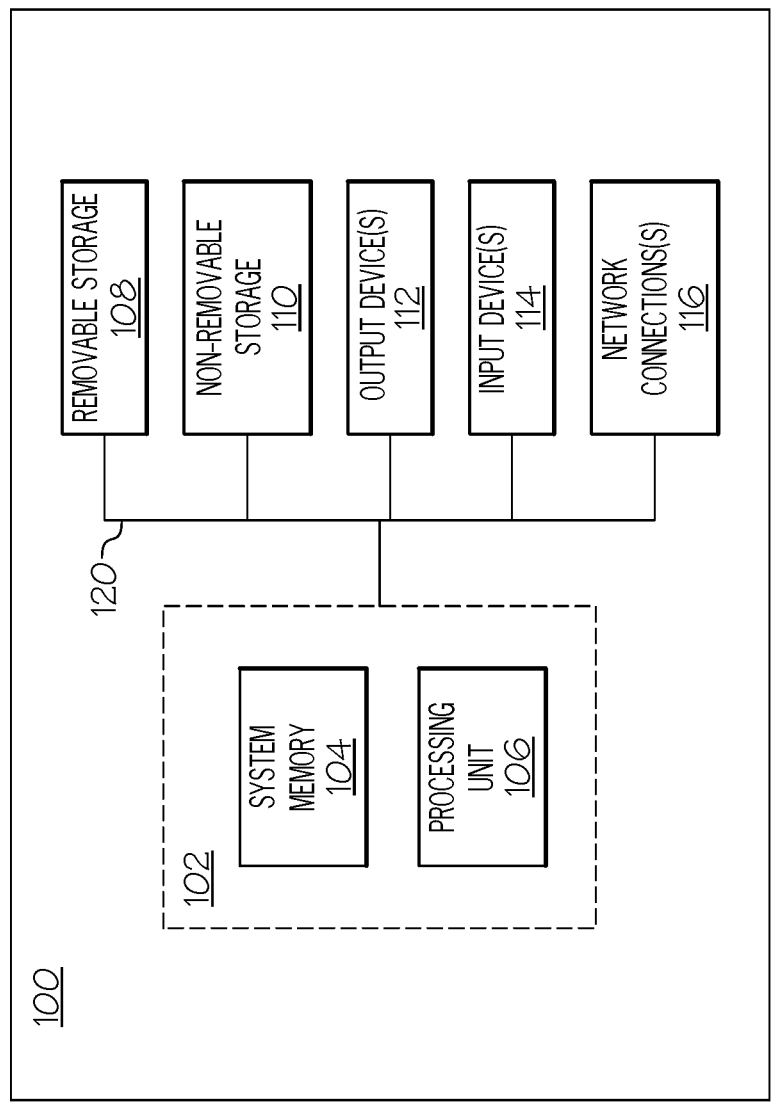
FIG. 1A depicts a computing device 100 according to one or more embodiments shown and described herein.

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented. Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1. Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Figure 2:
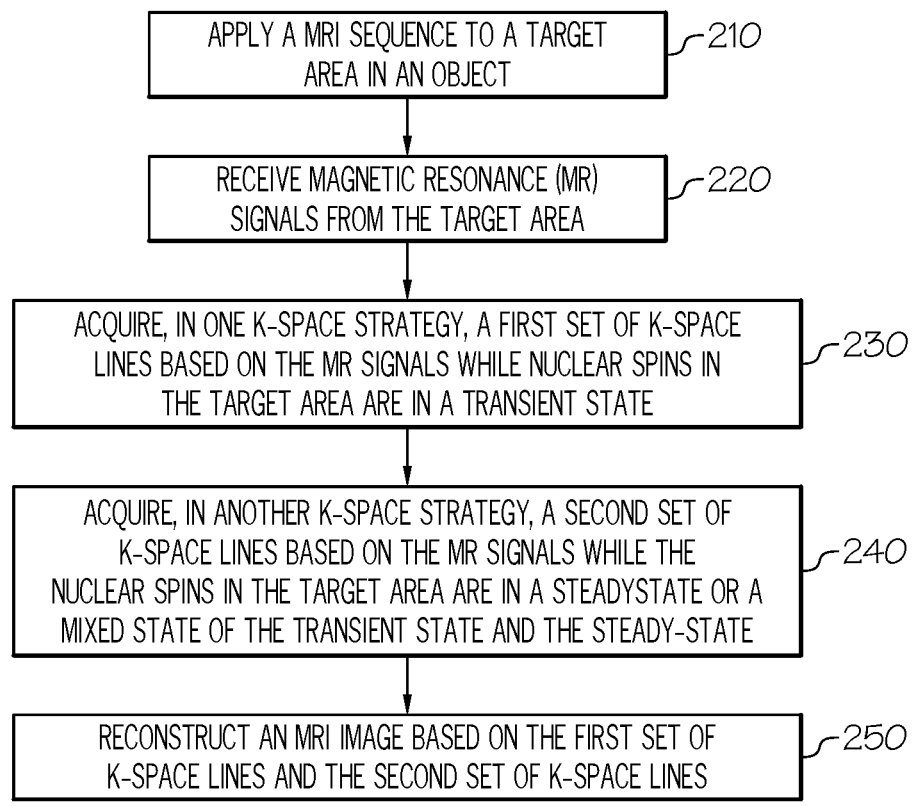
FIG. 2 is a flowchart for obtaining a high quality magnetic resonance imaging (MRI) image of an object according to one or more embodiments shown and described herein.

FIG. 2 is a flowchart for obtaining a high quality magnetic resonance imaging (MRI) image of an object according to one or more embodiments shown and described herein. In block 210, the MRI system 10 may apply a MRI sequence to a target area 18 in an object 9 shown in FIG. 1. In embodiments, the computing device 100 may instruct the gradient coil drivers 32 to activate the gradient magnetic field generating unit 14. The gradient magnetic field generating unit 14 generates gradient magnetic fields in an x-axis direction, a y-axis direction, and a z-axis direction to the target area 18 of the object 9 in FIG. 1. Applying the MRI sequence may further include using at least one of imaging techniques including at least one of parallel imaging technique, under-sampling technique including compressed sensing technique, or simultaneous multi-slice imaging technique. The MRI sequence may include, but not limited to, a gradient echo sequence, an echo planar sequence, a spin echo sequence, or variations of the gradient echo sequence, the echo planar sequence, or the spin echo sequence with or without magnetization preparation.

Referring still to FIG. 2, in block, 220, the MRI system 10 receives MR signals from the target area. In embodiments, the computing device 100 may receive MR signals from the receiving coil of the transmission and receiving unit 16 shown in FIG. 1.

In block 230, the MRI system 10 acquires, in one k-space strategy, a first set of k-space lines based on the MR signals while nuclear spins in the target area are in a transient state. The k-space strategy may be, but not limited to, a k-space sampling order, a k-space trajectory, a k-space under sampling, or a partial k-space acquisition. The k-space sampling order may be, but not limited to, at least one of a sequential sampling order, a centric sampling order, an interleave sampling order, a reverse sampling order, a random sampling order, or a hybrid sampling order. Examples of the k-space sampling order are described with reference to FIGS. 3A through 4C below.

Transient state indicated that the state of nuclear spin evolution in MRI experiments has been changed in a transient state before the state has not yet reached a steady state. The transient state of nuclear spin evolution always exists during the initial period of a sequence before steady-state evolution achieves from the initial condition. While nuclear spins are in a transient state, all k-space acquisitions have fluctuating longitudinal and transverse magnetization. As a result, each acquisition in the transient-state has different signal intensities. Transient state may exist in an echo train acquisition such as a series of radiofrequency pulses acquisition (e.g., MP-RAGE), refocusing radiofrequency pulse acquisition (e.g., fast echo spin), and bipolar gradient acquisition (e.g., echo planar imaging) at one repetition time interval. Also transient state can exist at the beginning of non-echo train acquisition, for example conventional gradient echo. Generally, the conventional gradient echo can reach the steady state when the gradient echo are acquired after several tens repetition time.

In block 240, the MRI system acquires, in another k-space strategy, a second set of k-space lines based on the MR signals while the nuclear spins in the target area are in a steady-state or a mixed state of the transient state and the steady-state. In embodiments, the MRI system may acquire the second set of k-space lines in a k-space strategy different from the k-space strategy used for acquiring the first set of k-space lines. For example, the first set of k-space lines are acquired with one k-space view sampling order (e.g., a sequential sampling order), and the second set of k-space lines are acquired with another k-space view sampling order (e.g., an interleave sampling order or center k-space view sampling order) or a combination of the k-space view sampling order and the another k-space view sampling order. In some embodiments, the MRI system may acquire the second set of k-space lines in a k-space strategy that is the same as the k-space strategy used for acquiring the first set of k-space lines.

Steady-state behavior appears because each radio-frequency pulse repetition time interval has the same gradient area and radiofrequency flip angle. While nuclear spins are in a steady-state case, all k-space acquisitions have the identical longitudinal and transverse magnetization. As a result, each acquisition in the steady-state has identical signal intensities when the effect of relaxation times is ignorable. According to embodiments of the present disclosure, the variation of nuclear magnetization in a transient state has been combined with optimal k-space acquisition to improve the image quality.

In block 250, the MRI system reconstructs the MRI image based on the first set of k-space lines and the second set of k-space lines. The first set of k-space lines may include k-space lines in the center of k-space (i.e. low spatial frequency components of k-space). The second set of k-space lines may include k-space lines in the periphery of k-space (i.e. high spatial frequency components of k-space). Longitudinal magnetization may achieve the steady-state after more than forty k-space lines are acquired. Traditionally, the periphery of k-space is acquired in the transient state before the longitudinal steady state is achieved. In contrast, according to present disclosure, k-space lines in the center of k-space are acquired while the nuclear spins are in the transient state and k-space lines in the periphery of k-space are acquired while the nuclear spins are in the longitudinal steady state. Because the MRI image is reconstructed based on k-space lines in the center of k-space in the transient state and k-space lines in the periphery of k-space in the longitudinal steady state, the MRI image has improved quality. The MRI system of the present disclosure provides MRI images having high signal and good contrast in short scan times compared to conventional MRI scanning.

Figures 3A, 3B:
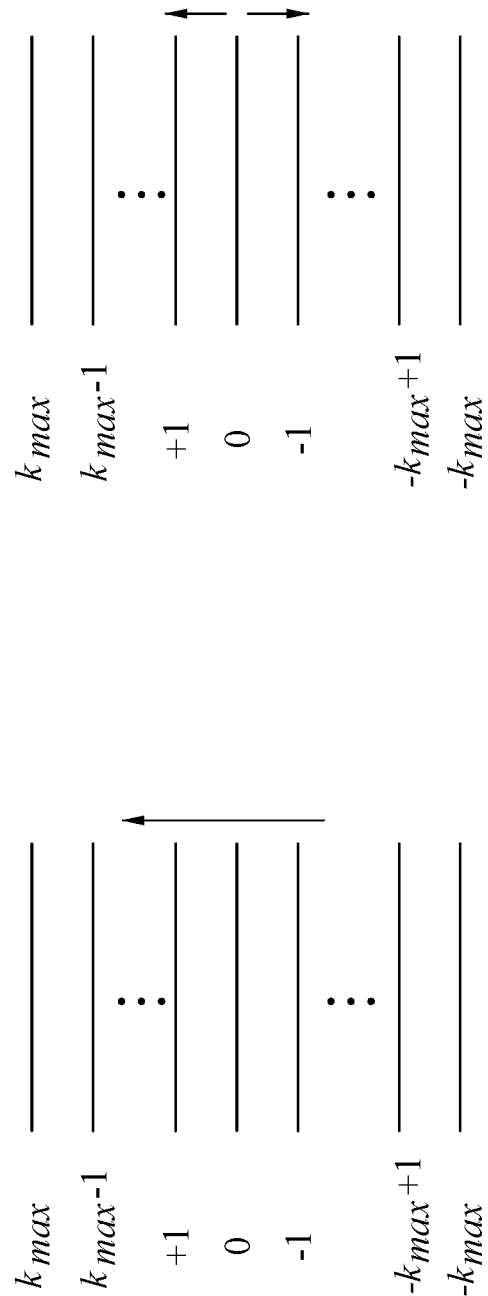
FIG. 3A depicts a sequential k-space view sampling schedule for MRI.
FIG. 3B depicts a central k-space view sampling schedule for MRI.

FIGS. 3A and 3B depict exemplary k-space view sampling schedules for MRI. FIG. 3A depicts a sequential k-space view sampling schedule for MRI. FIG. 3B depicts a central k-space view sampling schedule for MRI. If all k-space sampling are carried out in steady-state, the image quality for sequential and central k-space view sampling schedules would be completely identical. In practice, a transient state always exists in MRI acquisition because a large number of pulses are required to establish a steady state. The k-space acquisitions in the transient-state are used to reconstruct MRI images to avoid the reduction of MR efficiency when the acquisitions in the transient-state are removed. Additionally, the center of k-space includes the lower spatial frequencies, but no information about spatial details. That is, an image with low resolution and high contrast are reconstructed from the central k-space data. The peripheral regions of k-space contain the high spatial frequencies that are responsible for edges in the image data (tissue boundaries, for example) being well visible.

FIGS. 4A through 4C depict exemplary k-space view sampling schedules for MRI sequence with the partial Fourier acquisition. FIG. 4A depicts an example of sequential k-space view sampling schedules for MRI sequence with the partial Fourier acquisition. FIG. 4B depicts an example of central k-space view sampling schedules for MRI sequence with the partial Fourier acquisition. FIG. 4C depicts an example of hybrid k-space view sampling schedules for MRI sequence with the partial Fourier acquisition.

In FIGS. 4A through 4C, solid k-space lines are acquired k-space data and dashed k-space lines are synthesized data which are generated according to the Hermitian symmetry of the raw data in k-space. In embodiments, the acquisition of significant signal intensity at the central k-space may be carried out during longitudinal steady state in FIG. 4A. For example, k-space acquisition of MP-RAGE may be the sequential k-space view sampling.

In some embodiments, the acquisition of significant signal intensity at the central k-space is carried out during transient state as shown in FIG. 4B. For example, k-space acquisition of 3 dimensional Turbo field echo (TFE) in commercial Phillips scanner may be available by either the sequential k-space view sampling or the central k-space view sampling separately. In some embodiments, k-space strategy may be combined with multiple group k-space with different k-space sampling orders, or k-space trajectories and/or their combinations or hybrids. For example, multi-sequential k-space sampling view orders (from $-k_{max}$ to $+k_{max}$) may be classified into the sum of the first acquisition (from the beginning of k=0 to the end of k=$-k_{max}$) and the second acquisition (from the beginning of k=$+k_{max}$ to the end of k=1 or 0).

Example 1—Three Dimensional $T_1$-Weighted Brain Image Resolution in Clinical Practice It is noticed that some experiments according to the present disclosure can reach 1 mm isotropic resolution with the scan time of around 3 minutes at the cost of SNR efficiencies or image quality which strongly hinder the increase of spatial resolution. Their gray matter-white matter spatial CNR efficiency of is less than 0.4 per square root of second per mm³, while spatial SNR efficiency is less than 3 per square root of second per mm³ at 3.0 Tesla. The whole brain coverage image with 0.75 mm³ takes the total acquisition time of 7 minute 24 seconds at a 7.0 Tesla MRI scanner. The spatial SNR efficiency and spatial CNR efficiency for whole brain tissue are less than 1 and 0.28 per square root of second per mm³, respectively. However, gray matter-white matter spatial CNR efficiency is less than 1.7 per square root of second per mm³.

Figure 5:
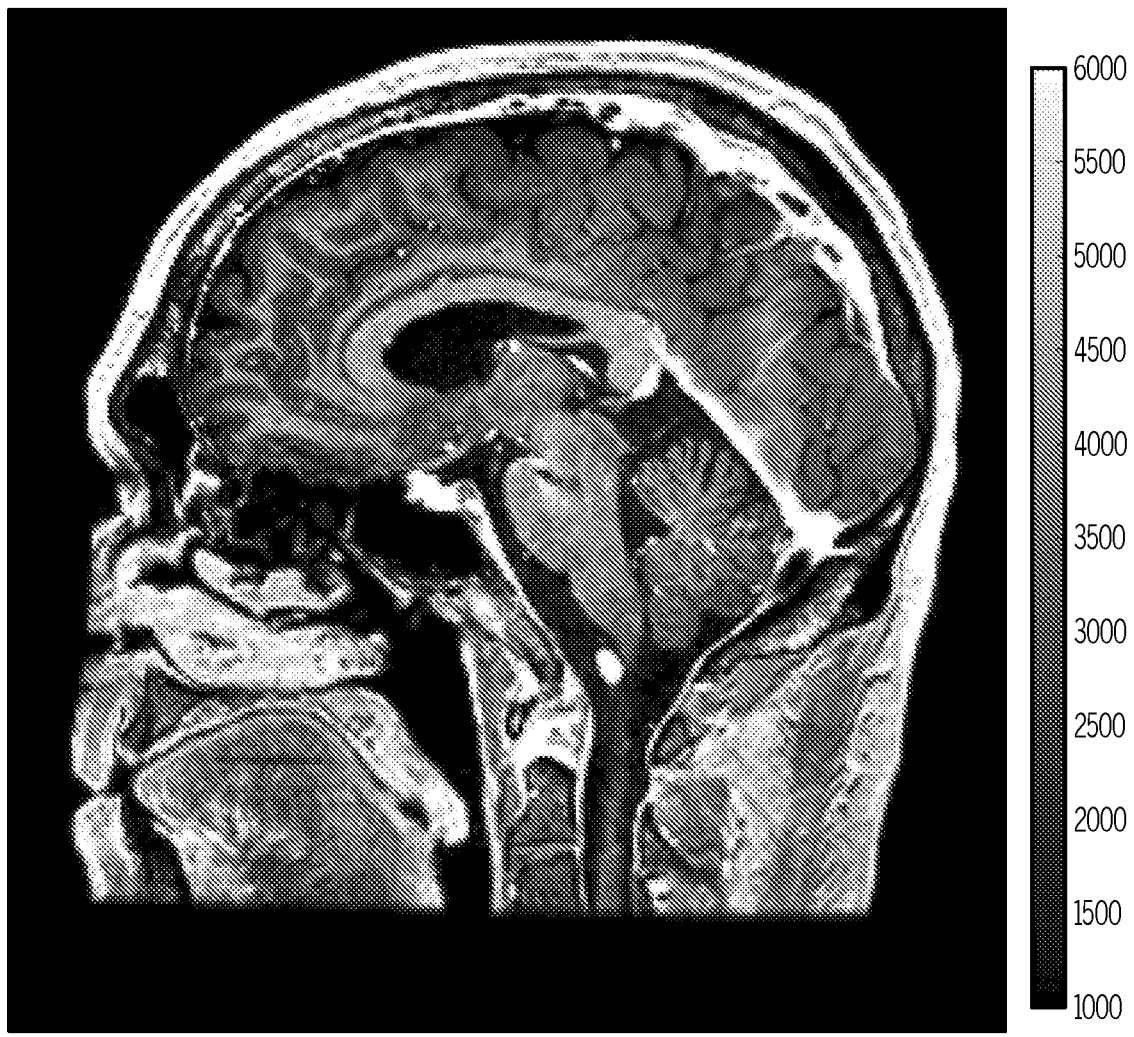
FIG. 5 depicts a brain image reconstructed from k-space data by Fourier transform. In embodiments, brain image of a healthy object is acquired with MP-RAGE sequence herein.

FIG. 5 depicts a brain image reconstructed from k-space data by Fourier transform according to one or more embodiments shown and described herein. In embodiments, brain image of a healthy object is acquired with MP-RAGE sequence herein. For example, k-space acquisition is divided into two partitions. In the first partition, the first 41 k-space lines are acquired with the central k-space view sampling order (e.g. kz=0, ±1, ±2 . . . ±20) at transient state of nuclear spins, and in the second partition, k-space lines are acquired by the reversal sequential k-space view sampling order with partial Fourier acquisition (e.g. kz=+kmax, kmax−1, . . . 21, 20). A hybrid k-space sampling ordering (e.g. combination of central k-space view and sequential k-space view sampling order) are used for acquiring high quality MRI images. Generally, MRI image resolution is proportional to the maximum k-space value and high resolution imaging usually requires high gradient amplitudes and/or long spatial encoding times. In FIG. 5, the isotropic resolution is 1 mm. The results indicate that the SNR and its efficiency are around 140 and 9.4 $s^{-1/2}$ for the brain images acquired with the optimized MP-RAGE sequence, and that the gray matter-white matter CNR and its efficiency are 26.5 and 1.7 $s^{-1/2}$ for the brain images acquired with the optimized MP-RAGE sequence. The slice spatial SNR efficiency for whole brain coverage image is around 0.74 per square root of second per mm³ per slice, and the gray matter-white matter slice spatial CNR efficiency is 0.13 per square root of second per mm³ per slice.

The spatial SNR efficiency for whole brain tissue is about 9.7 per square root of second per mm³, and gray matter-white matter spatial CNR efficiency is about 1.7 per square root of second per mm³. In embodiments, the hybrid k-space may extend to the combination of k-space sampling order, k-space trajectory, k-space under sampling, partial k-space acquisition and their combinations or hybrid. The k-space sampling in transient state and steady-state acquisitions may be completely different from, partially different from, or completely identical to each other, according to scanning sequence and objective being imaged.

Image quality may be evaluated by SNR, CNR, SNR efficiency, CNR efficiency, spatial-SNR efficiency, and spatial-CNR efficiency described herein. Additionally, image quality may also be evaluated by at least one of spatial-temporal resolution, coverage of the target region, artifact, and/or total scan time. The artifact may include, but not limited to, noise, signal inhomogeneity, SNR inhomogeneity, contrast inhomogeneity, CNR inhomogeneity, signal loss, geometry distortion or image ghost, or motion artifact.

Figure 6:
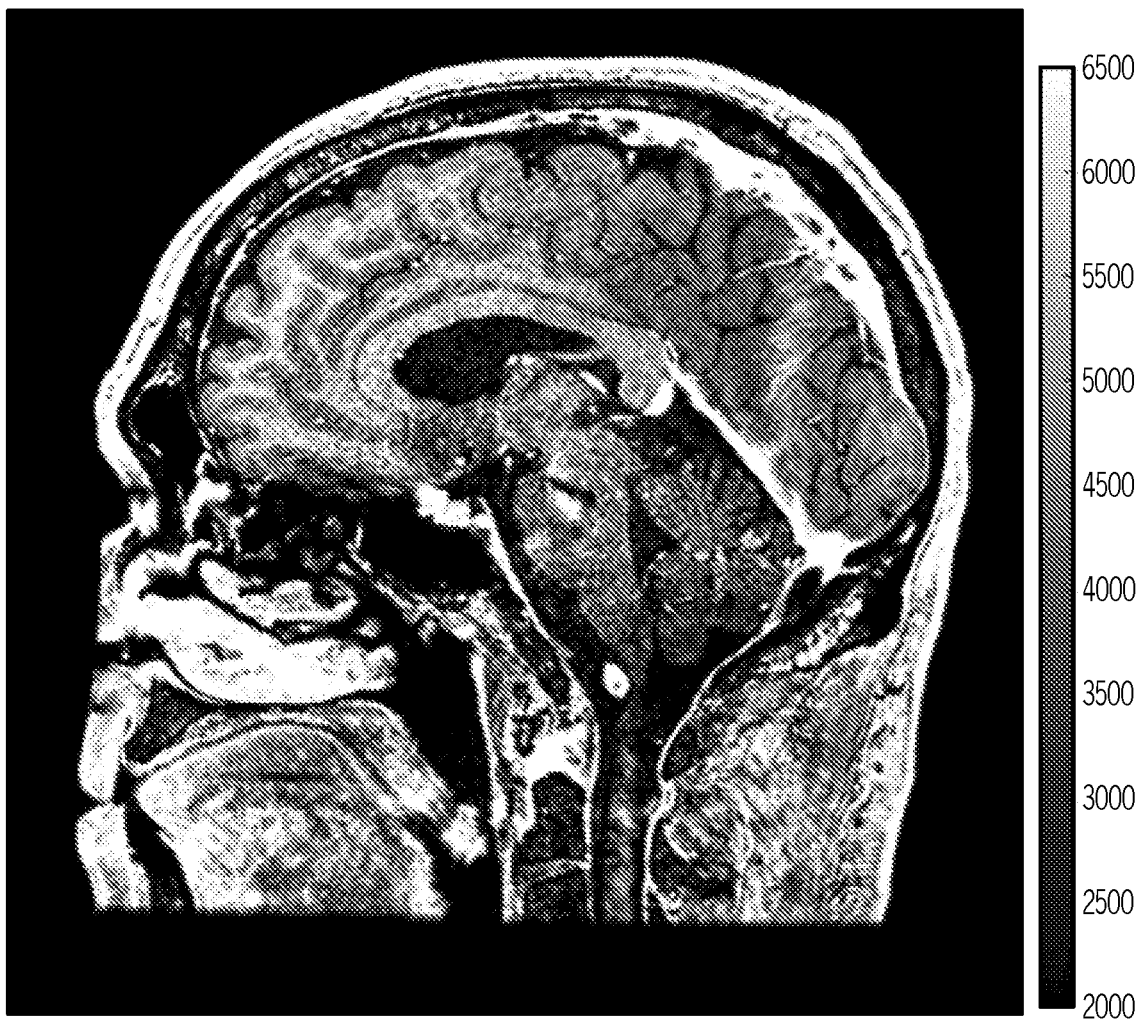
FIG. 6 depicts an example of brain image for a healthy object with the isotropic resolution of 0.6 mm acquired at 3.0 Tesla.

FIG. 6 depicts an example of brain image for a healthy object with the isotropic resolution of 0.6 mm acquired at 3.0 Tesla, according to one or more embodiments shown and described herein. The results indicate that the SNR and its efficiency are around 35 and 1.93 $s^{-1/2}$ for the brain images acquired with the optimized MP-RAGE sequence, and that the gray matter-white matter CNR and its efficiency are 6.6 and 0.36 $s^{-1/2}$ for the brain images acquired with the optimized MP-RAGE sequence. The spatial SNR efficiency for whole brain tissue is around 8.9 per square root of second per mm$^3$, and gray matter-white matter spatial CNR efficiency is 1.7 per square root of second per mm$^3$. The slice spatial SNR efficiency for whole brain coverage image is around 0.54 per square root of second per mm$^3$ per slice, and the gray matter-white matter slice spatial CNR efficiency is 0.104 per square root of second per mm$^3$ per slice. Compared with spatial SNR and CNR efficiencies of the isotropic resolution of 1.0 mm described above with reference to FIG. 5, the spatial SNR and CRN efficiencies in this example have a small reduction because of increasing total scan time. The SNR, CNR and their efficiencies have an apparent reduction because SNR and CNR are proportional to the size of voxel or pixel. Additionally, both the slice spatial SNR efficiency and the gray matter-white matter slice spatial CNR efficiency have an apparent reduction because of increased scan time and the number of slices.

In some embodiments, the k-space strategy can include a k-space trajectory and a sampling order. The k-space trajectory may include at least one of a rectilinear, radial, echo planar imaging, spiral, projection reconstruction, random, under-sampled, or partial k-space sampling trajectory, and their combinations or hybrid. The sampling order may include at least one of a sequential, centric, interleaved, reverse, or random sampling order, and their combinations or hybrid. In some embodiments, the MRI sequence may include at least one of a gradient echo sequence, echo planar sequence or spin echo sequence or their variations with or without magnetization preparation.

Example 2—Brain Tumor with High-Resolution Contrast Enhanced MRI

With improved diagnostic techniques, the number of newly diagnosed cases of brain metastases (BM) is growing, which currently is about 210,000 in the United States each year. Approximately 25-45% cancer patients develop this complication. Clinically, BM lesions are often diagnosed when they are sufficiently large to be detected on imaging. In later stage of tumor diagnosis, 1) the prognosis is extremely poor; 2) most potential therapies which may be effective at early stage fail to show their efficacy; and 3) the median survival is only about 3 months. Early stage diagnosis may lead to more treatment options to lengthen life of patients and increase quality of survival. Furthermore, early detection is beneficial to the development of new therapy agents and biomarkers developed for early detection can facilitate precise evaluation of response to therapy. Contrast enhanced magnetic resonance imaging (CE-MRI) may be considered as a gold standard technique for BM detection. Higher imaging resolution leads to better BM lesion detection sensitivity. However, contrast agent accumulation in lesions through blood-brain barrier permeability limits the confident detection of CE-MRI to only larger tumors (around 5-10 mm in diameter or $10^7$-$10^8$ BM cells). Meanwhile, animal studies show that tumor permeability to contrast agent is not associated with BM lesion size, aggressiveness, or growth duration, and CE-MRI could detect a BM lesion when ⅔ of MRI voxel accumulates gadolinium at 7.0 T MRI. These studies indicate that increasing spatial resolution should improve detection of small BM lesions, although translation of these techniques in routine clinical imaging is lacking. State-of-the-art clinical CE-MRI protocol currently recommends isotropic resolution of less than 1.5 mm at 3.0 T. However, high-resolution image acquisition results in increased acquisition time and reduced signal-to-noise ratio, hindering its clinical implementation. Although some potential biomarkers in preclinical studies may enable the detection of BM two to three orders of magnitudes smaller than is currently possible, further investigations are needed to prove their safety and feasibility in human.

Figure 7:
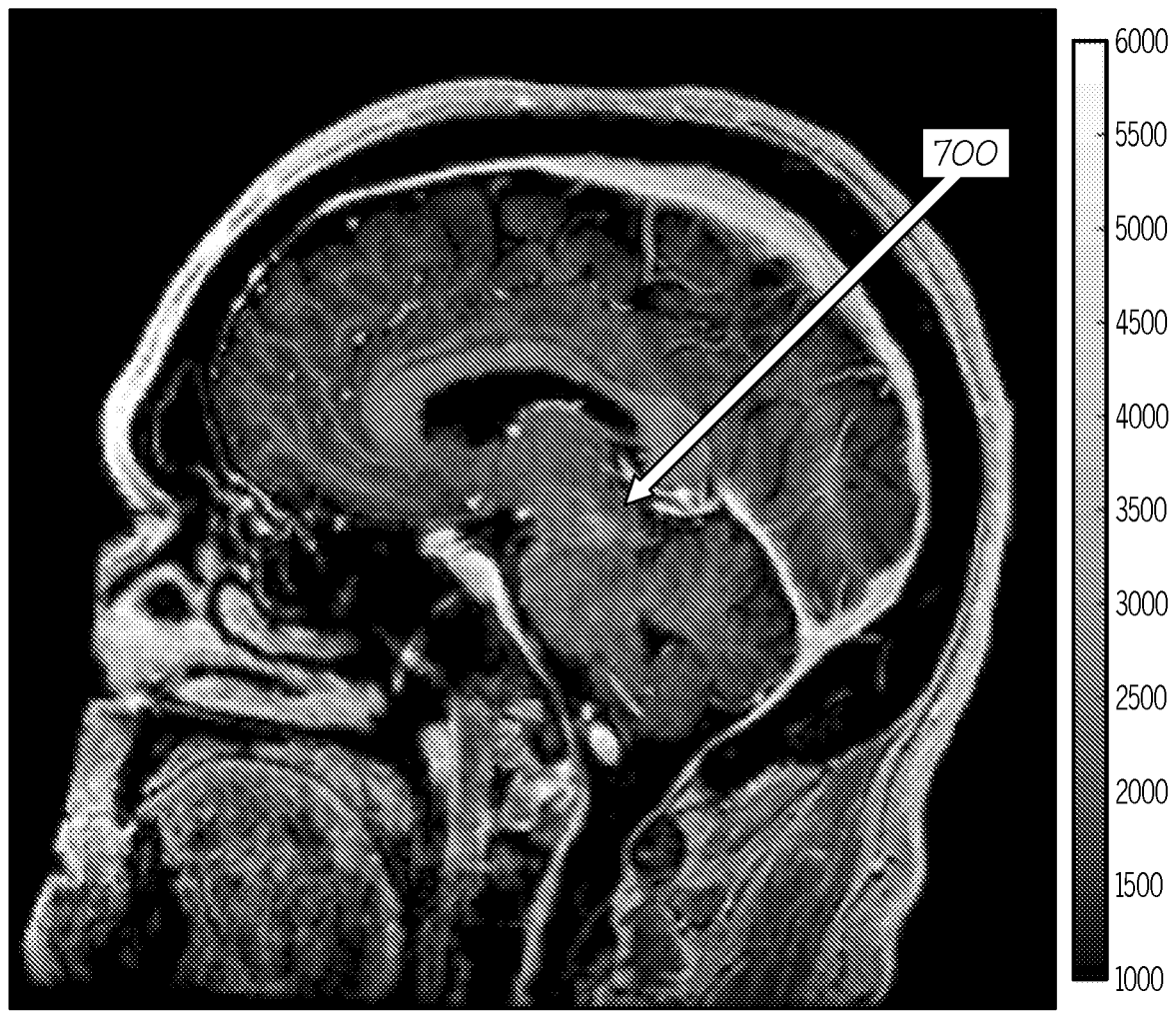
FIG. 7 depicts an example of brain image for a brain tumor patient with the isotropic resolution of 1 mm, according to one or more embodiments shown and described herein.

FIG. 7 depicts an example of brain image for a brain tumor patient with the isotropic resolution of 1 mm, according to one or more embodiments shown and described herein. The brain tumor 700 may be identified on the brain image. The brain image is acquired with the hybrid k-space at 3.0 Tesla. The results indicate that the SNR and its efficiency of enhanced tumor are about 148 and 12 s$^{-1/2}$ for the brain images acquired with the optimized MP-RAGE sequence, and that the tumor-brain tissue CNR and its efficiency are 57.3 and 4.7 s$^{-1/2}$ for the brain images acquired with the optimized MP-RAGE sequence. Their spatial SNR efficiency for whole brain tissue are around 12 per square root of second per mm$^3$, and the tumor-brain tissue spatial CNR efficiency is 4.7 per square root of second per mm$^3$. The slice spatial SNR efficiency for the enhanced tumor is around 11.7 per square root of second per mm$^3$ per slice, and the tumor-brain tissue CNR spatial CNR efficiency is 0.37 per square root of second per mm$^3$ per slice.

Figure 8:
FIG. 8 depicts an example of brain image for a brain tumor patient with the isotropic resolution of 0.7 mm, according to one or more embodiments shown and described herein.

FIG. 8 depicts an example of brain image for a brain tumor patient with the isotropic resolution of 0.7 mm, according to one or more embodiments shown and described herein. The brain tumor 800 may be identified on the brain image. The brain image is acquired with the hybrid k-space at 3.0 Tesla. The results indicate that the SNR and its efficiency of enhanced tumor are around 142 and 8.6 s$^{-1/2}$ for the brain images acquired with the optimized MP-RAGE sequence, and the tumor-brain tissue CNR and its efficiency are 88 and 5.4 s$^{-1/2}$ for the brain images acquired with the optimized MP-RAGE sequence. Their spatial SNR efficiency for enhanced tumor are around 414 per square root of second per mm$^3$, and the tumor-brain tissue spatial CNR efficiency is 15.7 per square root of second per mm$^3$. Compared with spatial SNR and CNR efficiencies of the isotropic resolution of 1.0 mm in FIG. 7, both spatial SNR and CNR efficiencies increase because of the reduction of partial volume effect. Particularly, the spatial SNR efficiency of enhanced tumor increases by 180%, and the spatial enhanced tumor-tissue CNR efficiency increases by 191%. The maximum spatial SNR efficiency of more than 414 per square root of second per mm$^3$, and maximum spatial tumor-tissue CNR efficiencies of more than 15.7 per square root of second per mm$^3$ are performed for enhanced tumor. The slice spatial SNR efficiency for the enhanced tumor is around 27.6 per square root of second per mm$^3$ per slice, and the tumor-brain tissue spatial CNR efficiency is 1.05 per square root of second per mm$^3$ per slice.

A system for a magnetic resonance imaging (MRI) image of an object is described herein. The system includes a magnetic field generating unit configured to apply a MRI sequence to a target area in the object, a receiver configured to receive MR signals from the target area, a processing unit, a system memory, and machine readable instructions stored in the system memory. The processing unit acquires, in one k-space strategy, a first set of k-space lines based on the MR signals while nuclear spins in the target area are in a transient state, acquires, in another k-space strategy, a second set of k-space lines based on the MR signals while the nuclear spins in the target area are in a steady-state or a mixed state of the transient state and the steady-state, and reconstructs the MRI image based on the first set of k-space lines and the second set of k-space lines.

A method for detecting small pathological and tiny structural changes using magnetic resonance imaging (MRI) of an object, is described herein. The method may include acquiring at least one image with high quality; differentiating pathological and tiny structural changes from normal physiological changes of the target region in the object based on the acquired image data; and characterizing pathological and structural changes. For example, the brain tumor 700 in FIG. 7 or the brain tumor 800 in FIG. 8 may be identified and characterized.

Modern MRI scanners used to acquire the MRI images may typically be configured to provide MRI images of internal features in an ROI of the body having spatial resolution as fine as 1 mm$^3$ (cubic millimeter). High-resolution MRI acquired in a reasonable time, has significantly enhanced the sensitivity of pathological changes. For example, high-resolution MRI can improve the detection sensitivity to BM detection, particularly for small nodules. The major challenge for high resolution, the image SNR reconstructed is extremely low. The present disclosure may obtain high resolution with reasonable image quality by the optimization of k-space acquisition strategy. In embodiments, the present disclosure applies hybrid k-space acquisition under transient and steady states to enhance image quality and improve detection sensitivity of path-physiological changes. Additionally, various k-space under-sampling techniques, such as compressed sensing, partial Fourier acquisition, a parallel imaging technique and/or their variations, provide various possibilities to implement the undersampling of k-space for improving image quality and reducing acquisition time.

In embodiments, the MRI image obtained according to the present disclosure has spatial SNR efficiency of more than 10 per square root of second per mm$^3$, or the slice spatial SNR efficiency of more than 0.4 per square root of second per mm$^3$ per slice, or a spatial lesion-tissue or tissue CNR efficiencies of more than 1.0 per square root of second per mm$^3$, or slice spatial lesion-tissue or tissue CNR efficiencies of more than 0.1 per square root of second per mm$^3$ per slice. In some embodiments, the MRI image obtained according to the present disclosure has spatial SNR efficiency of more than 60 per square root of second per mm$^3$, or the slice spatial SNR efficiency of more than 3.0 per square root of second per mm$^3$ per slice, or a spatial lesion-tissue or tissue CNR efficiencies of more than 4.0 per square root of second per mm$^3$, or slice spatial lesion-tissue or tissue CNR efficiencies of more than 0.4 per square root of second per mm$^3$ per slice. In some embodiments, the MRI image obtained according to the present disclosure has spatial SNR efficiency of more than 410 per square root of second per mm$^3$, or the slice spatial SNR efficiency of more than 20 per square root of second per mm$^3$ per slice, or a spatial lesion-tissue or tissue CNR efficiencies of more than 16.0 per square root of second per mm$^3$, or slice spatial lesion-tissue or tissue CNR efficiencies of more than 1.0 per square root of second per mm$^3$ per slice.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A method for obtaining a magnetic resonance imaging (MRI) image of an object, the method comprising:
   applying an MRI sequence to a target area in the object;
   receiving magnetic resonance (MR) signals from the target area;
   acquiring, in one k-space sampling order, a first set of k-space lines based on the MR signals while nuclear spins in the target area are in a transient state;
   after an acquisition of the first set of k-space lines, acquiring, in another k-space sampling order, a second set of k-space lines based on the MR signals while the nuclear spins in the target area are in a mixed state of the transient state and the steady-state, the one k-space sampling order being different from the another k-space sampling order;
   generating a third set of k-space lines according to Hermitian symmetry of the first set of k-space lines and the second set of k-space lines, the third set of k-space lines comprising one or more k-space lines in a periphery of k-space; and
   reconstructing the MRI image based on the first set of k-space lines, the second set of k-space lines, and the third set of k-space lines,
   wherein the one k-space sampling order is one of a sequential sampling order, a centric sampling order, an interleave sampling order, a reverse sampling order, a random sampling order, or a hybrid sampling order, and the another k-space sampling order is another of the sequential sampling order, the centric sampling order, the interleave sampling order, the reverse sampling order, the random sampling order, or the hybrid sampling order.

2. The method of claim 1, wherein the MRI sequence comprises at least one of a gradient echo sequence, an echo planar sequence, a spin echo sequence, or variations of the gradient echo sequence, the echo planar sequence, or the spin echo sequence with or without magnetization preparation.

3. The method of claim 1, wherein the first set of k-space lines are acquired with one k-space view sampling order, and the second set of k-space lines are acquired with another k-space view sampling order or a combination of the k-space view sampling order and the another k-space view sampling order.

4. The method of claim 1, wherein the first set of k-space lines and the second set of k-space lines are acquired with partial Fourier acquisition.

5. The method of claim 1, wherein applying the MRI sequence is applied using at least one of imaging techniques including at least one of parallel imaging technique, under-sampling technique including compressed sensing technique, or simultaneous multi-slice imaging technique.

6. The method of claim 1, wherein acquiring the first set of k-space lines includes acquiring a center of k-space, and acquiring the second set of k-space lines includes acquiring a periphery of k-space.

7. A system for obtaining a magnetic resonance imaging (MRI) image of an object, the system comprising:
   a magnetic field generating unit configured to apply an MRI sequence to a target area in the object;
   a receiver configured to receive MR signals from the target area;
   a processing unit;
   a system memory; and
   machine readable instructions stored in the system memory that, when executed by the processing unit, cause the processing unit to:
   acquire, in one k-space sampling order, a first set of k-space lines based on the MR signals while nuclear spins in the target area are in a transient state;
   after an acquisition of the first set of k-space lines, acquire, in another k-space sampling order a second set of k-space lines based on the MR signals while the nuclear spins in the target area are in a mixed state of the transient state and the steady-state, the one k-space sampling order being different from the another k-space sampling order;

generate a third set of k-space lines according to Hermitian symmetry of the first set of k-space lines and the second set of k-space lines, the third set of k-space lines comprising one or more k-space lines in a periphery of k-space; and reconstruct the MRI image based on the first set of k-space lines, the second set of k-space lines, and the third set of k-space lines, wherein the one k-space sampling order is one of a sequential sampling order, a centric sampling order, an interleave sampling order, a reverse sampling order, a random sampling order, or a hybrid sampling order, and the another k-space sampling order is another of the sequential sampling order, the centric sampling order, the interleave sampling order, the reverse sampling order, the random sampling order, or the hybrid sampling order.

8. The system of claim 7, wherein the MRI sequence comprises at least one of a gradient echo sequence, an echo planar sequence, a spin echo sequence, or variations of the gradient echo sequence, the echo planar sequence, or the spin echo sequence with or without magnetization preparation.

9. The system of claim 7, wherein the first set of k-space lines are acquired with one k-space view sampling order, and the second set of k-space lines are acquired with another k-space view sampling order or a combination of the k-space view sampling order and the another k-space view sampling order.

10. The system of claim 7, wherein the first set of k-space lines and the second set of k-space lines are acquired with partial Fourier acquisition.

11. The system of claim 7, wherein the MRI sequence is applied using at least one of imaging techniques including at least one of parallel imaging technique, under-sampling technique including compressed sensing technique, or simultaneous multi-slice imaging technique.

12. The system of claim 7, wherein acquiring the first set of k-space lines includes acquiring a center of k-space related to the MR signals, and acquiring the second set of k-space lines includes acquiring a periphery of k-space related to the MR signals.

13. A method for detecting pathological and/or structural changes using magnetic resonance imaging (MRI) of an object, the method comprising:

acquiring an MRI image of a target region in the object with the method according to claim 1;

differentiating pathological or structural changes from normal physiological changes of the target region or different physiological condition in the object based on the acquired MRI image respectively; and characterizing pathological or structural changes.

14. The method of claim 13, wherein the MRI image has spatial SNR efficiency of more than 10 per square root of second per $mm^3$, or slice spatial SNR efficiencies of more than 0.4 per square root of second per $mm^3$ per slice, or a spatial lesion-tissue or tissue CNR efficiencies of more than 1.0 per square root of second per $mm^3$, or slice spatial lesion-tissue or tissue CNR efficiencies of more than 0.1 per square root of second per $mm^3$ per slice.

15. The method of claim 14, wherein the MRI image has spatial SNR efficiency of more than 60 per square root of second per $mm^3$, or slice spatial SNR efficiencies of more than 3.0 per square root of second per $mm^3$ per slice, or a spatial lesion-tissue or tissue CNR efficiencies of more than 4.0 per square root of second per $mm^3$, or slice spatial lesion-tissue or tissue CNR efficiencies of more than 0.4 per square root of second per $mm^3$ per slice.

16. The method of claim 15, wherein the MRI image has spatial SNR efficiency of more than 410 per square root of second per $mm^3$, or slice spatial SNR efficiencies of more than 20 per square root of second per $mm^3$ per slice, or a spatial lesion-tissue or tissue CNR efficiencies of more than 16.0 per square root of second per $mm^3$, or slice spatial lesion-tissue or tissue CNR efficiencies of more than 1.0 per square root of second per $mm^3$ per slice.

17. The method of claim 1, wherein the MRI sequence is an echo planar sequence.

18. The system of claim 7, wherein the MRI sequence is an echo planar sequence.

* * * * *